United States Patent
Shaak et al.

(10) Patent No.: US 10,729,650 B2
(45) Date of Patent: Aug. 4, 2020

(54) SKIN PUNCH BIOPSY AND WOUND-DEBRIDGEMENT TRAINING MODEL

(71) Applicant: Government of the United States as Represented by the Secretary of the Air Force, Wright-Patterson AFB, OH (US)

(72) Inventors: Thomas Shaak, Ocean Springs, MS (US); Suizhao Wang, Biloxi, MS (US); Joseph Harre, D'Iberville, MS (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 401 days.

(21) Appl. No.: 15/875,571

(22) Filed: Jan. 19, 2018

(65) Prior Publication Data
US 2018/0211566 A1  Jul. 26, 2018

Related U.S. Application Data

(60) Provisional application No. 62/449,205, filed on Jan. 23, 2017.

(51) Int. Cl.
| | | |
|---|---|---|
| G09B 23/30 | (2006.01) | |
| A61K 9/127 | (2006.01) | |
| A61K 31/573 | (2006.01) | |
| A61K 31/565 | (2006.01) | |
| A61K 9/00 | (2006.01) | |
| A61P 35/00 | (2006.01) | |
| A61K 31/568 | (2006.01) | |
| A61K 47/10 | (2017.01) | |
| A61K 47/24 | (2006.01) | |

(Continued)

(52) U.S. Cl.
CPC .......... *A61K 9/1271* (2013.01); *A61K 9/0019* (2013.01); *A61K 31/565* (2013.01); *A61K 31/568* (2013.01); *A61K 31/573* (2013.01); *A61K 39/39* (2013.01); *A61K 47/10* (2013.01); *A61K 47/24* (2013.01); *A61M 1/0088* (2013.01); *A61P 35/00* (2018.01); *G09B 23/306* (2013.01); *G09B 23/34* (2013.01); *A61B 10/02* (2013.01); *A61B 17/32053* (2013.01); *A61B 2017/00707* (2013.01); *A61K 2300/00* (2013.01)

(58) Field of Classification Search
CPC .. A61K 9/1271; A61K 9/0019; A61K 31/565; A61K 31/568; A61K 31/573; A61K 39/39; A61K 47/10; A61K 47/24; A61K 2300/00; A61P 35/00; A61M 1/0088; G09B 23/306; G09B 23/34; A61B 10/02; A61B 17/32053; A61B 2017/00707
USPC ....................................................... 434/267
See application file for complete search history.

(56) References Cited

FOREIGN PATENT DOCUMENTS

| WO | 2007019546 | 2/2007 |
|---|---|---|
| WO | 2011009077 | 1/2011 |

OTHER PUBLICATIONS

V. R. Feezer et al., "Adrostenediol reverses steroid-inhibited would healing," Wound Repair and Regeneration, vol. 17 (2009) 758-761.

(Continued)

*Primary Examiner* — Robert P Bullington
(74) *Attorney, Agent, or Firm* — AFMCLO/JAZ; Chastity D. S. Whitaker

(57) ABSTRACT

A method of preparing a wound model. The method includes simulating a non-healing wound edge, simulating eschar, simulating a fibrin layer, simulating biofilm, and simulating foreign debris.

10 Claims, 9 Drawing Sheets

(51) Int. Cl.
    *A61K 39/39*     (2006.01)
    *A61M 1/00*     (2006.01)
    *G09B 23/34*     (2006.01)
    *A61B 10/02*     (2006.01)
    *A61B 17/3205*     (2006.01)
    *A61B 17/00*     (2006.01)

(56) References Cited

OTHER PUBLICATIONS

P. N. Huynh et al., "17 alpha androstenediol inhibition of breast tumor cell proliferation in estrogen receptor-positive and -negative cell lines," Cancer Detection and Prevention, vol. 24 (2000) 435-444.

R. A. Prough et al., "Effect of dehydroepiandrosterone on rodent liver microsomal, mitochondrial, and peroxisomal proteins," In: The Biologic Role of Dehydroepiandrosterone (DHEA), Ed: M. Kalimi, Walter de Gruyter (1990) Berlin, 253-279.

R. M. Loria et aL, "Regulation of the immune response by dehydroepiandrosterone and its metabolites," J. of Endocrinology, vol. 150 (1996) S209-S220.

A. Shai et aL, "Chapter 9: Debridement," In: Wound Healing and Ulcers of the Skin: Diagnosis and Therapy—The Practical Approach, Springer (2005) Berlin, 119-134.

A. S. Ulrich, "Biophysical aspects of using liposomes as delivery vehicles," Bioscience Reports, vol. 22 (2002) 129-150.

R. Voutilainen et al., "Hormonal regulation of P450scc (20, 22-desmolase) and P450c17 (17alpha-hydroxylase/17,20-lyase) in cultured human granulosa cells," J. Clinical Endocrinology and Metabolism, vol. 63 (1986) 202-207.

S. Tabiri, "Effectiveness of surgical skills training for surgical wound debridement using animal tissue as simulator," Postgrad. Med. J. Ghana, vol. 2 (2013) 3 pages total.

A. H. Dorafshar et al., "Guided surgical debridement: staining tissues with methylene blue," J. Burn Care & Res., vol. 31 (2010) 791-794.

M. Endara et al., "Using color to guide debridement," Adv. Skin & Wound Care, vol. 25 (2012) 549-555.

D. R. King et al., "Surgical wound debridement sequentially characterized in a porcine burn model with multispectral imaging," Burns, vol. (2015).

F. Smith et al., "Debridement for surgical wounds," Cochrane Library (2013) 23 pages total; available at http://onlinelibrary.wiley.com/doi/10.1002/14651858.CD006214.pub4/full;accessed Jan. 18, 2018.

T. J. Zuber et al., "Punch biopsy of the skin," Amer. Fam. Phys., vol. 65 (2002) 1155-1158.

U. Nischai et al., "Techniques of skin biopsy and practical considerations," J. Cutan Aesthet Surg., vol. 1 (2008) 107-111.

R. D. Wolcott et al., "Regular debridement is the main tool for maintaining a healthy wound bed in most chronic mounds," J. Wound Care, vol. 18 (2009) 54-56.

J. R. Wilcox et al., "Frequence of debridements and time to heal: a retrospective cohort study of 312744 wounds," JAMA Dermatol., vol. 149 (2013) 1050-1058.

J. D. Seltzer, "Skin biopsies in mammals," Clin. Techn., vol. 36 (2007) 23-24.

E. M. Skarlina et al., "Effectiveness of conventional and hydrosurgical debridement methods in reducing *Staphylococcus aureus* inoculation of equine muscle in vitro," Equine Vet. J., vol. (2014).

J. Dissemond et al., "Modern wound care—practical aspects of non-interventional topical treatment of patients with chronic wounds," J. Dtsch. Dermatol. Ges., vol. 12 (2014) 541-554.

B. M. Madhok et al., "New techniques for wound debridement," Int. Wound J., vol. 0 (2013) 247-251.

A. G. Nusbaum et al., "Effective method to remove wound bacteria: comparison of various debridement modalities in an in vivo porcine model," J. Surg. Res., vol. 176 (2012) 701-707.

J. Panuncialman et al., "The science of wound bed preparation," Surg. Clin. N. Am., vol. 89 (2009) 611-626.

K. Ousey et al., "Understanding wound bed preparation and wound debridement," Wound Care (2010) S22-S28.

C. Dowsett et al., "Time principles of chronic wound bed preparation and treatment," British J. Nursing: Tissue Viability Suppl, vol. 13 (2004) S16-S23.

A. Ghofrani et al., "The influence of systemic growth hormone administration on the healing time of skin graft donor sites in a pig model," Plast. Reconstr. Surg., vol. 104 (1999) 470-475.

L. Rosenberg et al., "Selectivity of a bromelain based enzymatic debridement agent: a porcine study," Burns, vol. 38 (2012) 1035-1040.

D. Leaper, "Sharp technique for wound debridement," World Wide Wounds (2002) 5 pages total.

S. Enoch et al., "Wound bed preparation: the science behind the removal of barriers to healing," Wounds, vol. 15 (2003) 6 pages total.

B. Gwynne et al., "An overview of the common methods of wound debridement," British J. Nursing, vol. 15 (2006) S4-S10.

A. F. Falabella, "Debridement and wound bed preparation," Derm. Ther., vol. 19 (2006) 317-325.

M. Granick et al., "Toward a common language: surgical wound bed preparation and debridement," Wound Repair & Regener., vol. 14 (2006) S1-S10.

I. Anderson, "Debridement methods in wound care," Nursing Stand., vol. 20 (2006) 65-72.

SKIN PUNCH BIOPSY AND WOUND-DEBRIDGEMENT TRAINING MODEL

Pursuant to 37 C.F.R. § 1.78(a)(4), this application claims the benefit of and priority to prior filed co-pending Provisional Application Ser. No. 62/449,205, filed Jan. 23, 2017, which is expressly incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to animal models and, more particularly, to animal models for educational and investigational uses.

BACKGROUND OF THE INVENTION

Delayed healing wounds cause morbidity, interfere with quality of life, create hardship for the patients, and create economic strain on the health care system. Skin biopsies are often necessary for diagnosis via histopathology examination and formation of treatment plan. Especially in the chronic wound condition, skin-punch biopsy provides evidence based on individual wound care. Debridement is crucial to wound healing. A slow healing wound tends to collect dead tissue or debrides (devitalized tissue may be eschar that is dry or leathery or slough that is soft and brown, grey, or yellow). The presence of necrotic or compromised tissue is common in chronic non-healing wounds.

Devitalized tissue provides a growth medium for bacteria, increasing infection risk and inflammation due to the influx of cytotoxic cells and products. The presence of cytotoxic cells and bacteria results in the release of fibroblasts and keratinocytes to the wound. Necrotic tissue prevents formation of granulation tissue, wound contraction, and epithelialization.

Chronic wounds are mired in a chronic inflammatory state, exhibiting markedly elevated pro-inflammatory cytokines, matrix metalloproteases, and excessive neutrophils. This persistent inflammatory state may be explained as the consequence of biofilm—chronic bacterial infection. The presence of compromised or necrotic tissue is common in chronic, non-healing wounds. The devitalized tissue provides a growth medium for bacteria, increases the risk of infection. Devitalized tissue releases endotoxins that inhibit migration of fibroblasts and keratinocytes to the wound, prevent the formation of granulation tissue, wound contraction, and epithelialization, are mired in a chronic inflammatory state exhibiting elevated pro-inflammatory cytokine, matrix metalloproteases, and excessive neutrophiles.

Debridement is the most effective modality to physical removal and suppression of biofilm reformation. However, complete eradication of biofilm with debridement is a major barrier for wound healing. Acute wounds may only require a single debridement; chronic wounds often require repeated debridement as slough continuous to reappear. Currently, there is no suitable chronic wound model to standardize the chronic wound debridement, especially for residencies or junior physicians training in wound care clinics.

With debridement being such an important technique necessary for wound care, it remains necessary to continually develop new training methods and models for providing surgical residents with test subjects.

SUMMARY OF THE INVENTION

The present invention overcomes the foregoing problems and other shortcomings, drawbacks, and challenges of existing models of wound care. While the invention will be described in connection with certain embodiments, it will be understood that the invention is not limited to these embodiments. To the contrary, this invention includes all alternatives, modifications, and equivalents as may be included within the spirit and scope of the present invention.

According to an embodiment of the present invention, a method of preparing a wound model that includes simulating a non-healing wound edge, simulating eschar, simulating a fibrin layer, simulating biofilm, and simulating foreign debris.

Other embodiments of the present invention are directed to a method of preparing a wound model that includes creating a wound on a surface of a specimen. A non-healing wound edge is simulated by applying an orange dye to the surface of the specimen that is adjacent to the wound. Slough is simulated by applying orange dye to a wound bed of the wound. Eschar is simulated by applying a black dye to the wound bed of the wound. A fibrin layer is simulated by applying a yellow dye to the wound bed of the wound. Biofilm is simulated by applying a mixture comprising yellow orange dye, bright blue dye, yellow green dye, and a tissue adhesive to the wound bed of the wound. Foreign debris is simulated by introducing fabric pieces into the wound Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
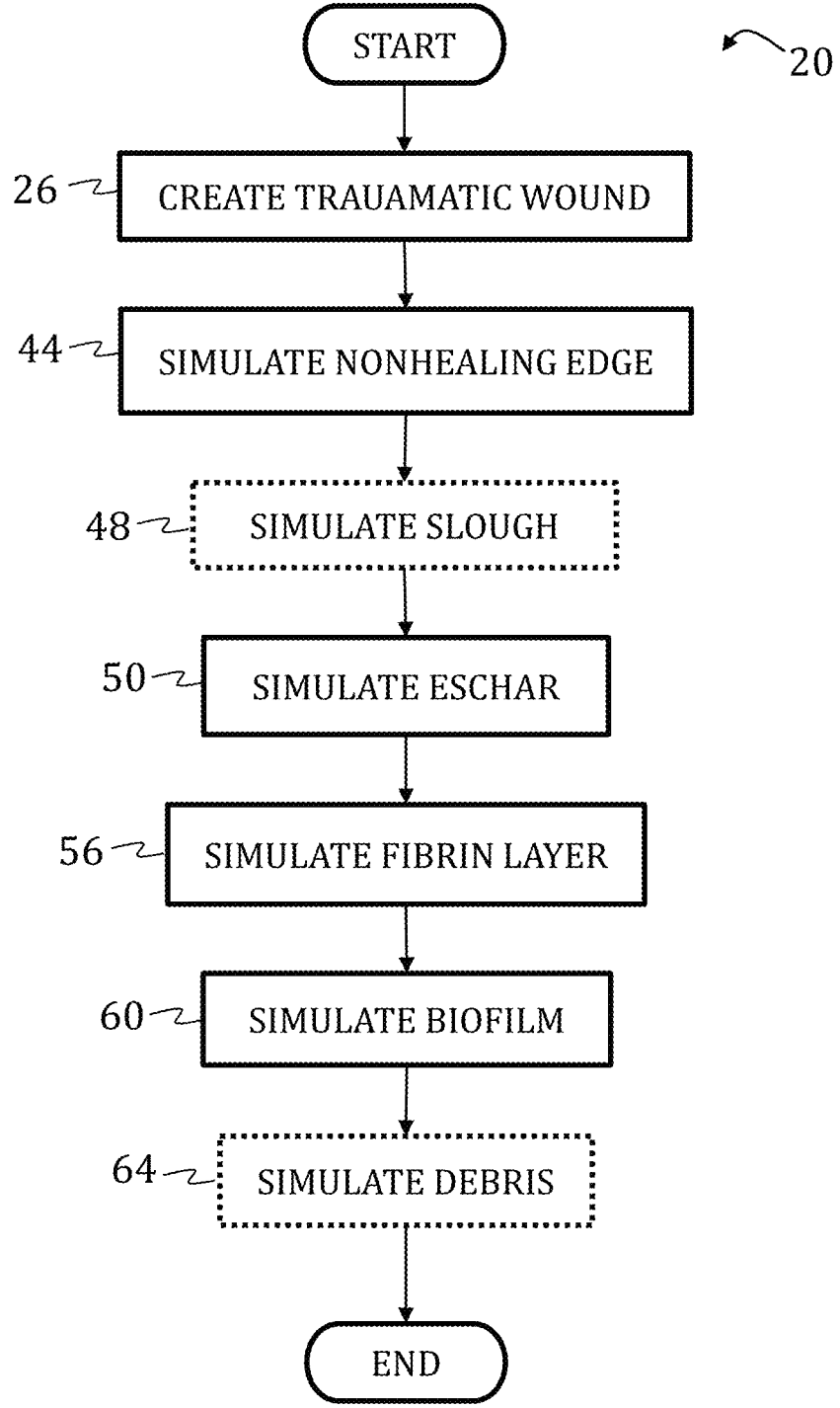
FIG. 1 is a flowchart illustrating a method of preparing a wound model according to an embodiment of the present invention.

Turning now to the figures, and in particular to FIG. 1 with reference to FIGS. 2-4G, a flow chart 20 illustrating a method of preparing a wound model according to an embodiment of the present invention is shown. While any mammal may be used, for purposes of illustration herein, a specimen 22 from *Sus scrofa* is shown. However, specimen may be selected from the group of mammals consisting of *Mus musculus, Rattus norvegicus, Mesocricetus auratus, Cavia porcellus, Oryctolagus cuniculus, Sus scrofa, Capra hircus, Ovis aries, Bos aurus, Canis familiaris, Felis catus,* and *Mucaca mulatta*.

At start, a surgically-created traumatic wound 24 is made in the specimen 22 (Block 26). While the wound 24 may be created on any surface of the specimen 22, preferably, the wound 22 may be created on a leg 28, 30, the back (not shown), the chest 32, or the neck 34 of the specimen, the latter of which is illustrated herein. The wound 24 may be created in any known manner, such as by scalpel 36 (illustrated), razor blade, and so forth such that a clean incision is created.

Figure 2:
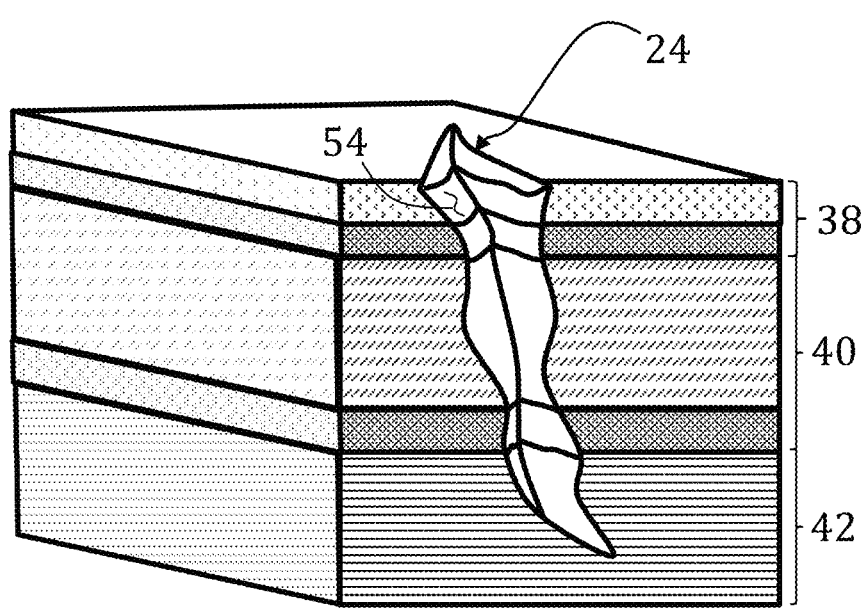
FIG. 2 is a side-elevational view, in cross-section, of a block of tissue having a surgically-created traumatic wound therein.
Figure 3:
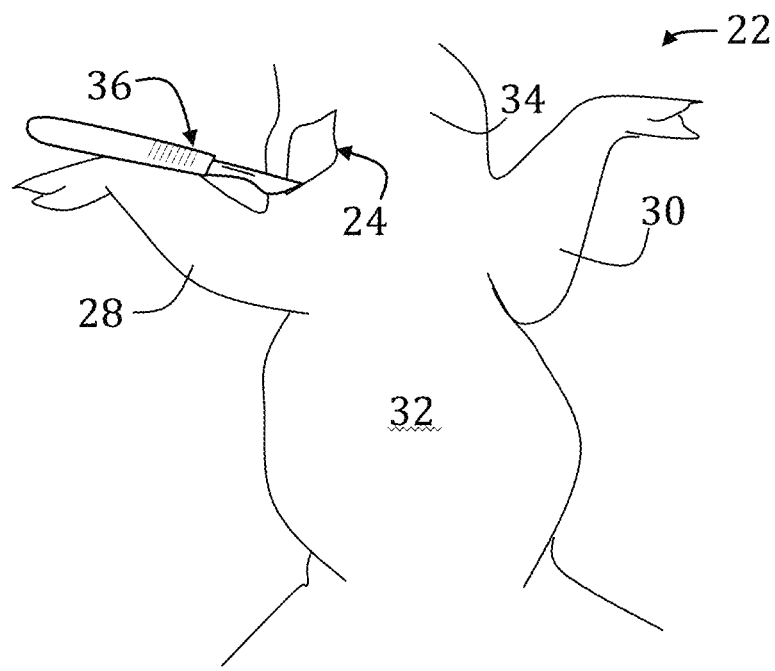
FIG. 3 is a top view of a porcine subject having a surgically-created traumatic wound according to an embodiment of the present invention.

Dimensions of the wound 24 (illustrated in both FIG. 3 and FIG. 4A) may vary, but may generally range in length from 5 cm to about 15 cm and in depth from 0.20 cm to about 1.00 cm. For example, as shown in FIG. 2, the wound may extend into outer skin layers 38 (including epidermal and dermal layers), into fat layers 40 (hypodermal layer and subcutaneous fat), or into muscle layers 42.

In Block 44, a non-healing wound edge is simulated by applying an orange dye (Polysciences, Inc.) to an area 46 of about 0.5 cm width around an edge of the wound 24. The orange dye may also be applied, if desired, to an area 47 the wound bed 54 for simulating slough, in optional Block 48.

Figure 4A:
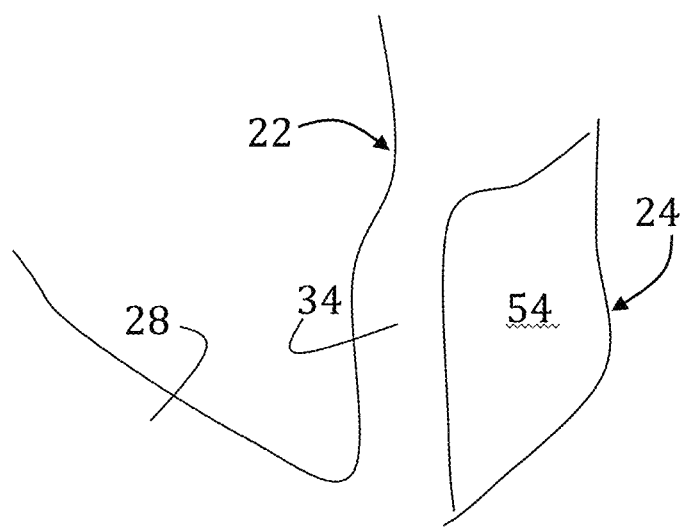
FIGS. 4A-4G are enlarged, sequential top views of the preparation of a wound model in the surgically-created traumatic wound in the porcine subject of FIG. 3.
Figure 4B:
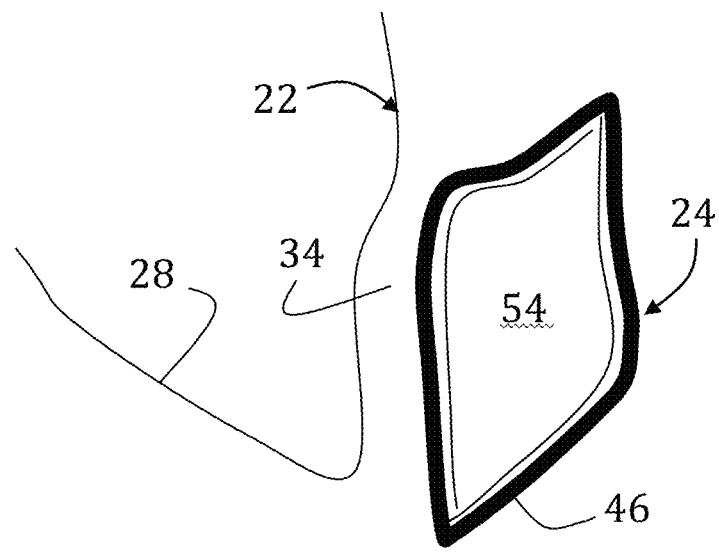
Figure 4C:
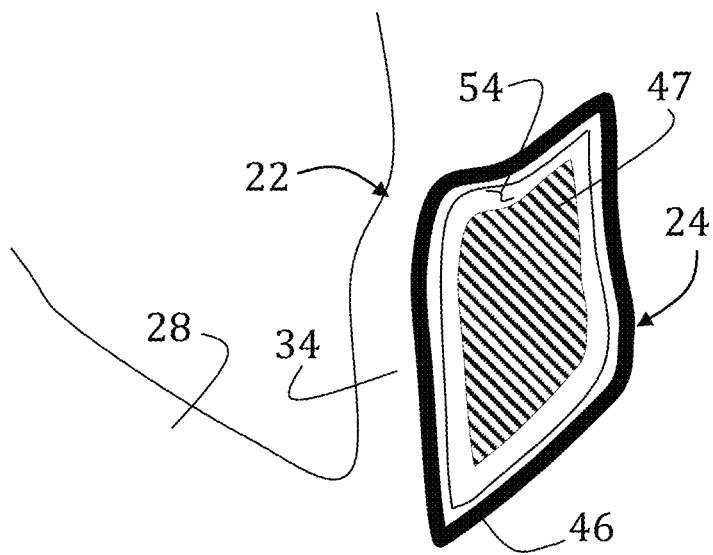
Figure 4D:
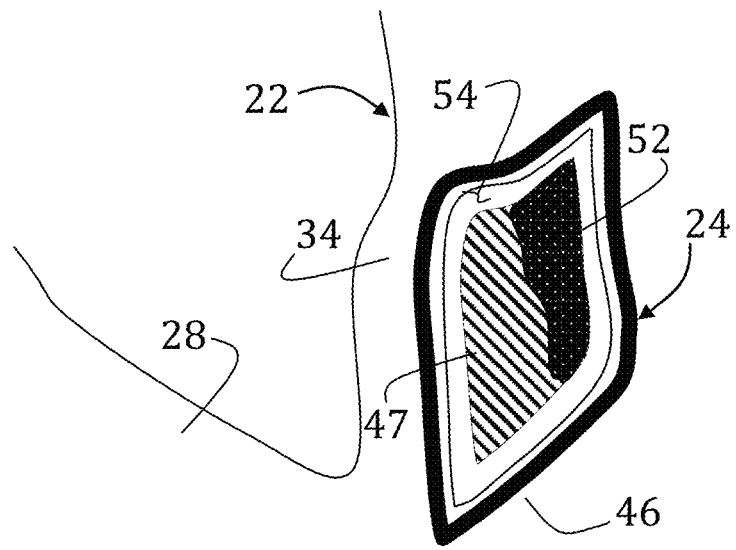
Figure 4E:
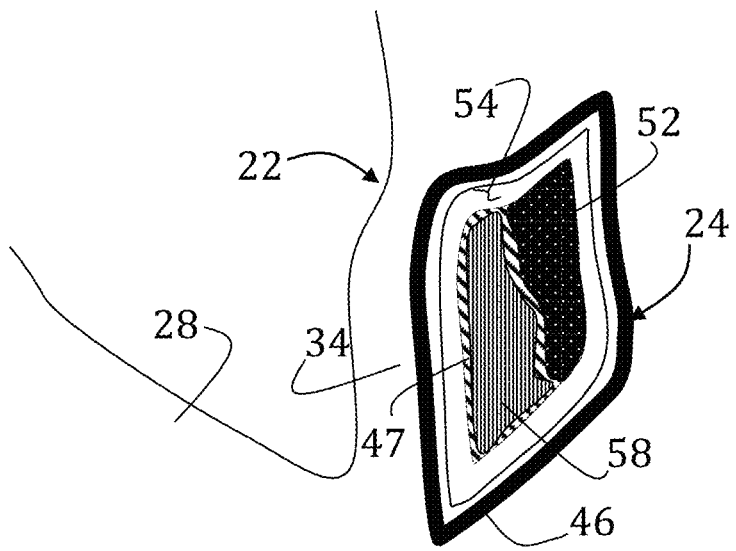

In Block 50, and as shown in FIG. 4D, black dye (Polysciences, Inc.) may be applied to an area 52 of the wound bed 54 to simulate eschar (see FIG. 4C). In Block 56, yellow dye (Polysciences, Inc.) may be applied to an area 58 of the wound bed 54 to simulate a fibrin layer, as shown in FIG. 4E.

Figure 4F:
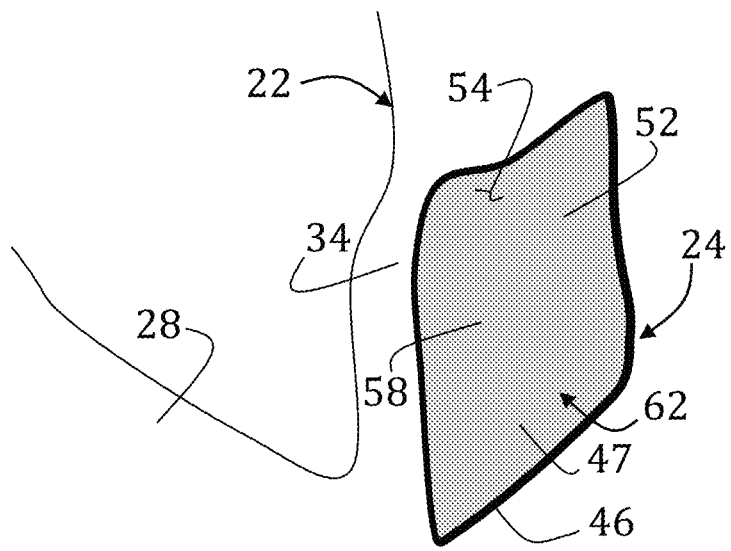
Figure 4G:
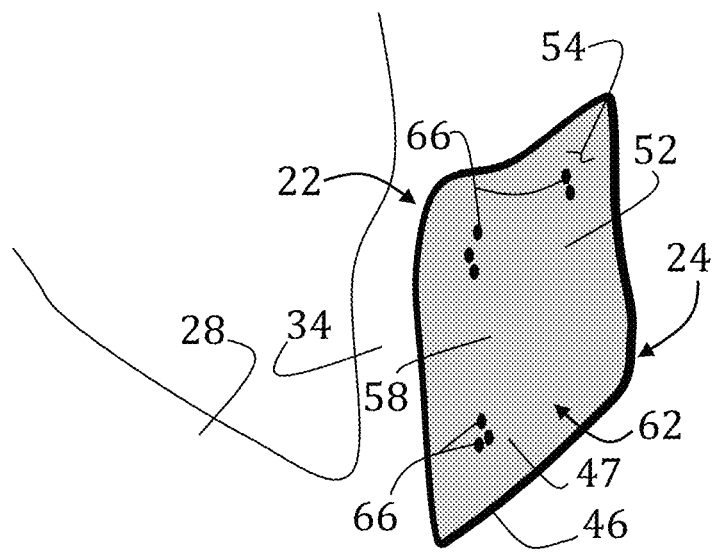

Simulation of biofilm, Block 60 and illustrated in FIG. 4F, may including applying a mixture of 0.2 µm Yellow Orange (YO), 1.0 µm Bright Blue (BB), and 2.0 µm Yellow Green (YG) Fluoresbrite carboxylate microspheres (Polysciences, Inc.) and LiquiVet Tissue Adhesive (Oasis Medical, Inc.) to an area 62 that may include the entire wound bed 54 or only a portion thereof.

If desired, wound simulation may be completed by optionally introducing fabric pieces to simulate foreign debris 66 (Block 54).

Figure 5:
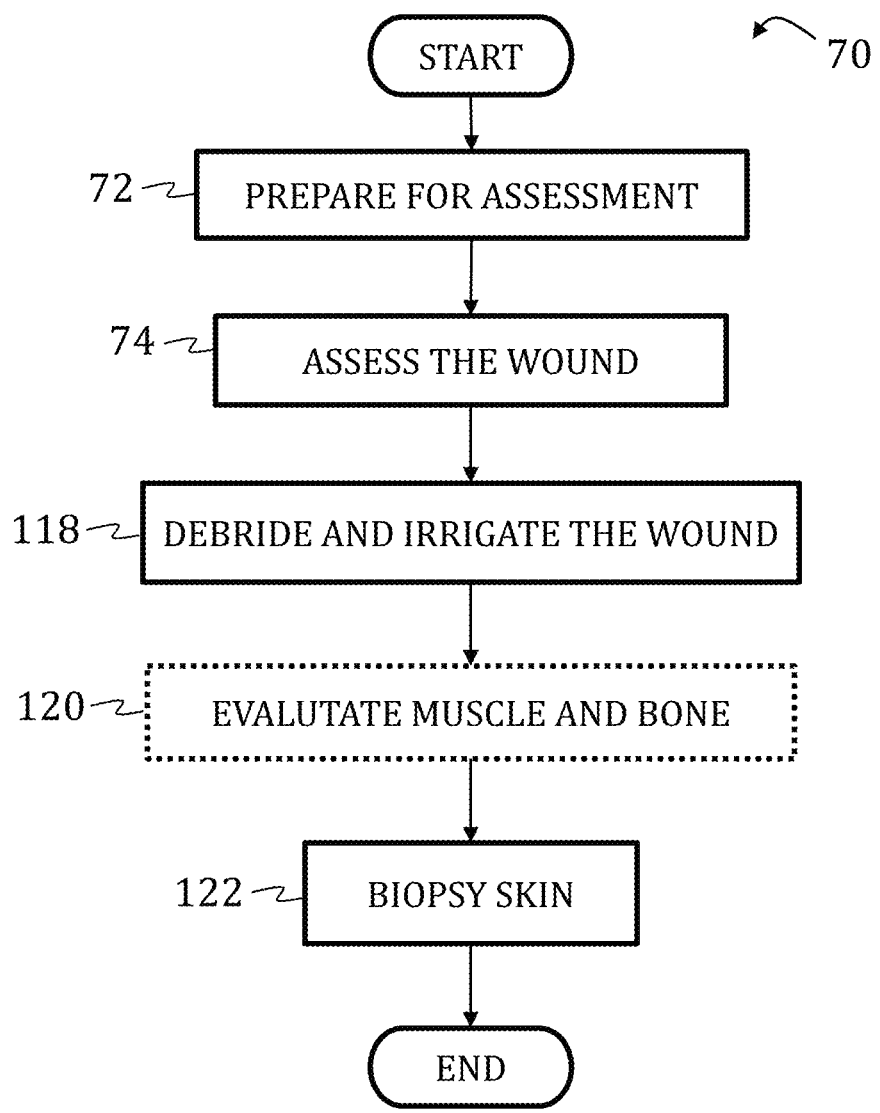
FIGS. 5-5B are flowcharts illustrating a method of cleaning a wound model prepared in accordance with embodiments of the present invention.

Turning now to FIG. 5, a flow chart 70 illustrating a method of wound assessment and debridement according to an embodiment of the present invention is shown. At start in Block 72, suitable materials and tools should be prepared for the assessment. Such materials may extend to those that would be necessary in the event of bleeding, including but not limited to gauze and topical gelfoam agents.

Figure 5A:
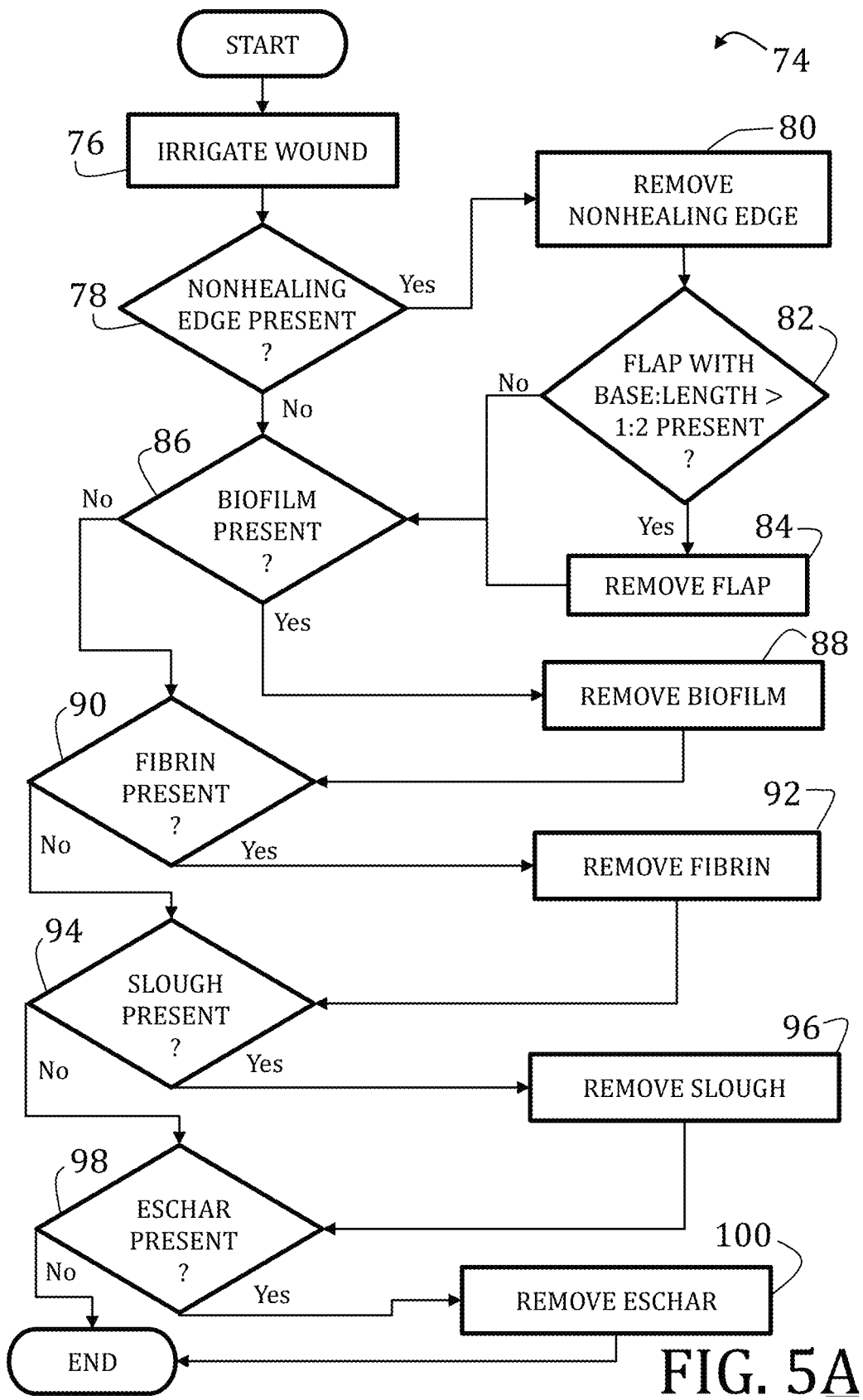

In Block 74, the wound 24 is generally assessed. Such assessment is illustrated in greater detail with the flow chart 76 of FIG. 5A, with reference still to FIG. 4G. As such, the wound 24 may be irrigated with sterile saline solution or water, such that the wound may be clearly assessed (Block 76). If an orange edge 46 is present (i.e., representing a non-healing edge 46) (Decision Block 78), then the non-healing edge 46 should be removed ("Yes" branch of decision block 78; Block 80); otherwise ("No" branch of decision block 78), assessment continues. The non-healing edge 46 may be sharply excised, as much as possible, while avoiding normal (i.e., unstained) skin.

If a traumatic skin flap associated with the non-healing edge 46 is present (Decision Block 82), and a base-to-length ratio of the flap exceeds more than 1:2, then the flap should also be sharply excised ("Yes" branch of decision block 82; Block 84). If necessary, extension of the wound 24 may be made in the direction of a long axis of the limb (if the wound 24 is on the specimen's limb). If extensions across flexor creases are necessary, then such extensions should be completed to be obliquely to prevent contractures. Otherwise ("No" branch of decision block 82), assessment continues.

Continuing with wound assessment 74, and if biofilm is present (Decision Block 86), indicated by a green shiny layer 62 in the wound bed 54, then the biofilm should be removed ("Yes" branch of decision block 86; Block 88); otherwise ("No" branch of decision block 86), assessment continues.

If a fibrin layer is present (Decision Block 90), indicated by a thin yellow layer 58 in the wound bed 54, then the fibrin layer should be removed ("Yes" branch of decision block 90; Block 92); otherwise ("No" branch of decision block 90), assessment continues.

If slough is present (Decision Block 94), indicated by debris 66 representing stringy, wet, dense, clinging dead matter in the wound bed 54, then the slough should be removed ("Yes" branch of decision block 94; Block 96); otherwise ("No" branch of decision block 94), assessment continues.

If an eschar layer is present (Decision Block 98), indicated by smooth, dense dead skin tissue in the wound bed (as compared to rough scab of dried blood and exudate), then the eschar layer should be removed ("Yes" branch of decision block 98; Block 100).

Figure 5B:
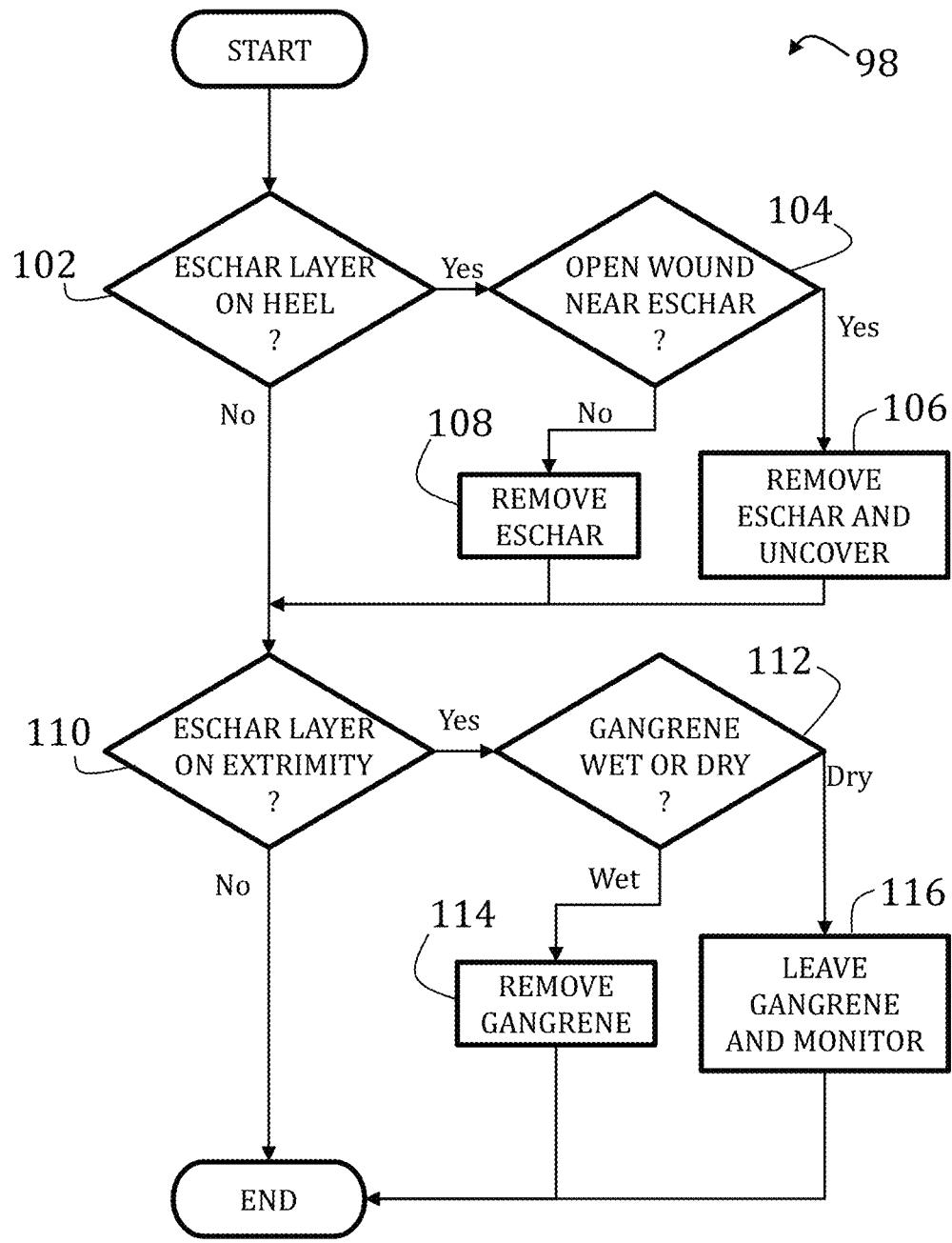

Referring now to FIG. 5B, further evaluation of the eschar layer is illustrated. At start, if the eschar layer is found on a heel of the specimen 22 (FIG. 2) ("Yes" branch of decision block 102) with no open areas around it ("No" branch of decision block 104), then the layer may, optionally, be removed or remain uncovered (Block 106), and assessment continues. Otherwise ("No" branch of decision blow 104), the eschar layer should be removed (Block 108) and the assessment continues. If no eschar layer is present ("No" branch of decision block 102), then the assessment continues without need for removal.

If black or brown spots thought to be eschar are present ("Yes" branch of decision block 110) on an extremity, particularly on the toes, then such may be gangrene. If gangrene is wet ("Wet" branch of decision block 112), then immediate surgery may be required (Block 114); otherwise, if the gangrene is dry ("Dry" branch of decision block 112), then the gangrene may be monitored (Block 116). Otherwise, ("No" branch of decision bock 110), the assessment continues.

Referring again to FIG. 5, the method 70 continues with removal of tissue and foreign debris and further irrigation of the wound 24 (Block 118). Debridement may be accomplished with conventional surgical instruments, such as scalpels, scissors, and forceps (not specifically illustrated). The wound 24 may then be irrigated with sterile saline solution or water.

Wound debridement may, optionally, include shaving a superficial upper layer of the wound bed may be performed with a scalpel for a fine curette. According to a preferred embodiment, the curette may be used to accurately outline the chronic would margin and to remove associated layers.

In removing dead or decaying tissue, debris, and so forth, great care should be taken as marginal peripheral epithelialization may be stimulated. As such, newly formed epithelium should not be damaged.

With debridement complete, the wound may again be irrigated with sterile sale solution or water.

If necessary, such as the wound 24 being sufficient in death, or desired, muscle, other subcutaneous tissue, and bone may be evaluated (Block 120). While not specifically illustrated, such evaluation may include the removal of damaged subcutaneous tissue and fascia may be sharply excised. Complete fasciotomies should be performed for compartments with elevated intracompartmental pressure. In evaluating muscle, conventional indicators may be used, such as color, consistency, contractility, and capacity to bleed.

If necessary, bone ends may be delivered for adequate debridement. Generally, open wounds that penetrate a joint capsule will require arthrotomy and irrigation of the intraarticular space. If tissue is available for closure, bone fragments lacking periosteum or soft tissue attachments are debrided. Major articular fragments should be retained regardless of soft tissue attachments if the joint is to be salvaged.

In Block 122, skin and tissue associated with the wound 24 may be biopsied. While not specifically illustrate, biopsies should be sampled from each of the wound bed 54, the wound edge (within 0.25 cm of the wound 24), and surrounding, undamaged skin (less than 1.5 cm from the wound 24) by preparing the area with disinfectant (for example 2% chlorhexidine gluconate and 70% isopropyl alcohol) and anesthetic (such as EMLA cream or lidocaine jelly).

Tension lines proximate the wound are identified, and the region proximate to the wound is stretched in a direction that is generally perpendicular to a line of least tension. A punch biopsy is collected during applied tension by holding a biopsy tool normal to the surface to the sampled. The biopsy tool is rotated downward, in a twirling motion until a desired depth is achieved (dermis, subcutaneous fat, or instrument hub, for example). The biopsy tool is removed and the biopsy wound permitted to bleed. When the area is released from tension, the biopsy wound may be elliptical in shape and aligned with lines of least tension.

Excess blood may be wiped from the biopsy wound and appropriate gauze or other material applied to facilitate clotting. If necessary, nylon or other appropriate suture may be used to close the biopsy wound. A direction of suturing should be oriented parallel to the line of least tension.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of preparing a wound model, the method comprising:
    simulating a non-healing wound edge;
    simulating eschar;
    simulating a fibrin layer;
    simulating biofilm; and
    simulating foreign debris.
2. The method of claim 1, further comprising:
    creating a wound on a surface of a specimen.
3. The method of claim 2, wherein simulating a non-healing wound edge comprises:
    applying an orange dye to the surface of the specimen that is adjacent to the wound.
4. The method of claim 3, further comprising:
    simulating slough by applying orange dye to a wound bed of the wound.
5. The method of claim 2, wherein simulating eschar comprises:
    applying a black dye to a wound bed of the wound.
6. The method of claim 2, wherein simulating the fibrin layer comprises:
    applying a yellow dye to a wound bed of the wound.
7. The method of claim 2, wherein simulating biofilm comprises:
    applying a mixture comprising yellow orange dye, bright blue dye, yellow green dye, and a tissue adhesive to a wound bed of the wound.
8. The method of claim 7, wherein the yellow orange dye, the bright blue dye, and the yellow green dye are microsphere dyes.
9. The method of claim 2, wherein simulating foreign debris comprises:
    introducing fabric pieces into the wound.
10. A method of preparing a wound model, the method comprising:
    creating a wound on a surface of a specimen;
    simulating a non-healing wound edge by applying an orange dye to the surface of the specimen that is adjacent to the wound;
    simulating slough by applying orange dye to a wound bed of the wound;
    simulating eschar by applying a black dye to the wound bed of the wound;
    simulating a fibrin layer by applying a yellow dye to the wound bed of the wound;
    simulating biofilm by applying a mixture comprising yellow orange dye, bright blue dye, yellow green dye, and a tissue adhesive to the wound bed of the wound; and
    simulating foreign debris by introducing fabric pieces into the wound.

* * * * *